United States Patent [19]

Pavlich

[11] Patent Number: 4,460,644
[45] Date of Patent: Jul. 17, 1984

[54] POLYURETHANE FOAM IMPREGNATED WITH OR COATED WITH FABRIC CONDITIONING AGENT, ANTI-MICROBIAL AGENT AND ANTI-DISCOLORANT

[75] Inventor: Mary J. Pavlich, Morristown, N.J.

[73] Assignee: Beecham Inc., Clifton, N.J.

[21] Appl. No.: 453,221

[22] Filed: Dec. 27, 1982

[51] Int. Cl.³ ............................. B32B 9/00; B05D 3/12
[52] U.S. Cl. ........................................ 428/314.4; 34/9; 427/242; 428/305.5; 428/320.2
[58] Field of Search ............... 428/305.5, 320.2, 314.4, 428/314.8; 34/60, 9; 252/106; 427/242

[56] References Cited

U.S. PATENT DOCUMENTS

| | | |
|---|---|---|
| 4,110,498 | 8/1978 | Benjamin et al. ................. 428/320.2 |
| 4,167,594 | 9/1979 | Schwadtke et al. ................ 427/242 |
| 4,170,565 | 10/1979 | Flesher et al. .................... 428/305.5 |
| 4,259,373 | 3/1981 | Demessemaekers et al. ...... 427/242 |
| 4,297,406 | 10/1981 | Metcalfe et al. .................. 427/242 |
| 4,389,448 | 6/1983 | Green ............................... 427/242 |

*Primary Examiner*—William J. Van Balen
*Attorney, Agent, or Firm*—Jacobs & Jacobs

[57] ABSTRACT

Fabric conditioning articles for use in an automatic laundry dryer are prepared comprising a polyurethane foam substrate impregnated with or coated with an effective amount of a fabric conditioning agent, an anti-microbially effective amount of a halide ion-containing agent and an anti-discoloration effective amount of zinc sulfate, sorbitol or dextrose.

40 Claims, No Drawings

POLYURETHANE FOAM IMPREGNATED WITH OR COATED WITH FABRIC CONDITIONING AGENT, ANTI-MICROBIAL AGENT AND ANTI-DISCOLORANT

The use of fabric conditioning articles which comprise a polyurethane foam substrate impregnated with a fabric softener and/or anti-static agent thereby entrapping or entraining said agent within the cellular structure of the foam is known. Cling Free ® (trademark of Beecham Inc.) is such a dryer-added fabric softener and anti-static article which is co-mingled with clothes to be rendered soft and/or substantially static-free in an automatic laundry dryer during the drying cycle.

When fabric conditioning articles which comprise a polyurethane foam substrate impregnated with or coated with a fabric softener and/or anti-static agent have incorporated therein an anti-microbially effective amount of a halide ion-containing agent, discoloration of the foam which naturally occurs over time is accelerated. While discoloration of the foam is preliminarily only an aesthetic disadvantage, it is also an early indicator that detrimental foam deterioration will occur later on. The present invention is based on the discovery that the rate of discoloration can be effectively reduced by incorporating into said agent an anti-discoloration effective amount of zinc sulfate, sorbitol or dextrose. Thus, a fabric conditioning article according to the present invention which comprises a polyurethane foam substrate impregnated with or coated with a fabric softener and/or antistatic agent which has incorporated herein an anti-microbially effective amount of halide ion-containing agent and an anti-discoloration effective amount of zinc sulfate, sorbitol or dextrose provides all the advantages of the prior art (the clothes are rendered soft and substantially static-free) together with deodorizing properties from the anti-microbial agent and the rate of foam discoloration is dramatically reduced. Unpigmented white foam typically discolors to yellow over time. The more typically used polyurethane foam which contains a blue or green pigment shows discoloration toward green or brown, respectively, over time.

The instant invention is thus particularly advantageous for retarding the discloration of blue and green polyurethane foams in the presence of halide ion-containing anti-microbial agents but can also be used to retard the discoloration of other polyurethane foams including unpigmented white polyurethane foams in the presence of said anti-microbial agents. The instant invention has been found to be particularly advantageous for retarding the discoloration of polyurethane foams in the presence of chloride or bromide ion-containing anti-microbial agents, and particularly chloride ion-containing anti-microbial agents. Since the fabric softener may be a quaternary ammonium compound in the halide form the presence of halide ions in the quaternary ammonium compounds would be expected to have a similar effect on the foam. Therefore, if such a quaternary ammonium compound is used together with a halide ion-containing anti-microbial agent such as a chloride or bromide ion-containing anti-microbial agent, it may be necessary to increase the amount of zinc sulfate, sorbitol or dextrose beyond that range which is useful when the only halide ion-containing source is the anti-microbial agent.

While the halide ion-containing anti-microbial agent may be a chloride, bromide or iodide ion-containing anti-microbial agent, particularly useful anti-microbial agents according to the present invention are the chloride and bromide ion-containing anti-microbial agents and in particular, chloride ion-containing anti-microbial agents have been found to be particularly suitable according to the present invention.

While the polyurethane foam substrate is preferably a flexible open-celled polyurethane foam, in which case the impregnation results in entrapping or entraining the active system within the cellular structure of the foam, a substantially closed-cell polyurethane foam could also be used with the active system being coated onto one or both of the surfaces of the foam. In addition to the fabric softening and/or anti-static agent, the active system would include an anti-microbially effective amount of a halide ion-containing anti-microbial agent and an anti-discoloration effective amount of zinc sulfate, sorbitol or dextrose.

The instant invention has been found to be particularly useful when flexible open-celled polyurethane foam having a water absorbant capacity of about 15–30, preferably 15–20, times its weight in water is used as the substrate and the active system is entrapped or entrained within the cellular structure of the foam.

While any suitable fabric softening and/or anti-static agent may be incorporated into or onto the polyurethane foam substrate, particularly useful agents include a mixture comprising 50–99% by weight of a cationic fabric softener and 1–50% by weight of a non-ionic surfactant selected from the group consisting of polyoxyethylene fatty acid esters, polyoxyethylene fatty alcohol esters and polyoxypropylene fatty acid esters.

According to a further embodiment of the present invention, the cationic fabric softener is present in an amount of 50–90%, preferably 65–75%, of the fabric softening mixture. The amount of non-ionic surfactant must be sufficient to lower the melting point of the cationic/non-ionic fabric softener mixture to within the temperature range of an automatic dryer during the drying cycle. The non-ionic surfactant is present in an amount of 10–50%, preferably 25–35%, of the fabric softening mixture. It may also be necessary to depart somewhat from the above ranges of cationic to non-ionic agents, depending on the particular nature of the cationic fabric softener, the non-ionic surfactant, the thickness of the foam substrate being used, the nature of the anti-microbial agent and the specific anti-discoloration agent used. One preferred weight ratio of cationic fabric softener to non-ionic surfactant is from about 1:1 to 9:1. A range of 1:1 to 2.3:1 has been found to be a particularly useful range and depending upon the thickness of the foam, a ratio of 2.3:1 may be especially suitable. Again, depending upon the selection of specific cationic fabric softener and non-ionic surfactant, a ratio of 70:30 may be particularly useful, again depending upon the thickness of the foam and other ingredients used. When a thinner foam is used, a desirable ratio is about 85:15.

The polyoxyethylene fatty acid esters, the polyoxyethylene fatty alcohol esters and the polyoxypropylene fatty acid esters preferably have 12 to 18 carbon atoms in the fatty chain. Those having an even number of carbon atoms in the fatty chain are particularly preferred. Among the non-ionic surfactants which have been found to be useful are:

Polyoxyethylene (4) lauryl ether
Polyoxyethylene (2) oleyl ether
Polyethylene glycol 200 monooleate Polyethylene glycol 400 dioleate
Polyethylene glycol 200 monostearate
Polyethylene glycol 600 monostearate
Useful cationic quaternary ammonium salts include:
Dodecyltrimethyl ammonium chloride
Didodecyldimethyl ammonium chloride
Tetradecyltrimethyl ammonium chloride
Ditetradecyldimethyl ammonium chloride
Pentadecyltrimethyl ammonium chloride
Dipentadecyldimethyl ammonium chloride
Didodecyldiethyl ammonium chloride
Didodecyldipropyl ammonium chloride
Ditetradecyldiethyl ammonium chloride
Ditetradecyldipropyl ammonium chloride
Ditallowdiethyl ammonium chloride
Ditallowdipropyl ammonium chloride
Tallowdimethyl benzyl ammonium chloride
Tallowdiethyl benzyl ammonium chloride
Dodecyltrimethyl ammonium methyl sulfate
Didodecyldiethyl ammonium acetate
Tallowtrimethyl ammonium acetate
Tallowdimethyl benzyl ammonium nitrite
Ditallowdipropyl ammonium phosphate
Tallowtrimethyl ammonium chloride
Tallowdimethyl (3-tallowalkoxypropyl)ammonium chloride
Ditallow dimethyl ammonium chloride
Ditallow dimethyl ammonium methyl sulfate
Eicosyltrimethyl ammonium chloride
Dieicosyldimethyl ammonium chloride
Methyl-1-coco amido ethyl-2-coco imidazolinium methyl sulfate
Methyl-1-soya amido ethyl-2-soya imidazolinium methyl sulfate
Methyl-1-tallow amido ethyl-2-tallow imidazolinium methyl sulfate
Methyl-1-oleyl amido ethyl-2-oleyl imidazolinium methyl sulfate
Methyl-1-tallow amido ethyl-2-tallow imidazolinium chloride
Di-(hydrogenated tallow) dimethyl ammonium methyl sulfate
Distearyldimethyl ammonium methyl sulfate
Dipalmityl dimethyl ammonium methyl sulfate and
Dibehenyl dimethyl ammonium methyl sulfate.

The cationic fabric softener is preferably a quaternary ammonium fabric softener, particularly a quaternary ammonium fabric softener in the methyl sulfate form.

Preferred cationic fabric softeners are dialkyl dimethyl ammonium methyl sulfates selected from the group consisting of di-(hydrogenated tallow) dimethyl ammonium methyl sulfate, distearyl dimethyl ammonium methyl sulfate, dipalmityl dimethyl ammonium methyl sulfate and dibehenyl dimethyl ammonium methyl sulfate.

The anti-discoloration effective amount of zinc sulfate is preferably from about 0.2 to about 2% by weight based on the total weight of finished product. About 0.5% has been found to be a particularly useful amount. The anti-discoloration effective amount of sorbitol or dextrose is preferably from about 2 to 6% by weight based on the total weight of finished product. About 4% has been found to be particularly suitable.

Various additives may also be utilized in the compositions of the present invention. Perfumes, whitening agents, shrinkage controllers, spotting agents, fungicides, fumigants, anti-creasing agents, finishing agents, lubricants, sizing agents and the like may be added to the composition. When included in the composition, these additives will generally be added in the amount of from 0.01% to 10% by weight of the total active systems. Examples of useful additives may be found in any current yearbook of the American Association of Textile Chemists and Colorists. Any additive utilized should, of course, be compatible with the cationic fabric softener, the non-ionic surfactant, the foam substrate, the anti-microbial agent, the anti-discoloration agent, the fabrics and the dryer.

While not essential, liquids which serve as a carrier for the softening mixture of the present invention can also be employed as part of the compositions of the present invention. Such liquids can be used to impregnate or coat the substrate more evenly with the cationic fabric softener and the non-ionic surfactant. Such a liquid carrier should be inert and compatible with the cationic fabric softener, the non-ionic surfactant, the foam substrate, the anti-microbial agent, the anti-discoloration agent, the fabrics and the dryer.

Moreover, the liquid carrier when so used should be one which substantially evaporates. Isopropyl alcohol or isopropyl alcohol/water mixtures are suitable liquid carriers for substrate impregnation purposes.

Preferred polyurethane foams should also have a degree of thermal stability so that the foam with the cationic fabric softener and the non-ionic surfactant, anti-microbial agent and zinc sulfate, sorbitol or dextrose entrained or entrapped within the cellular structure will maintain its integrity at operating dryer temperatures and not be subject to deformation, distortion, melting or disintegration.

A convenient thickness for the polyurethane foam has been found to be approximately 0.085 inches, although other thicknesses can be used. It has also been found convenient to cut the foam into sheets and those approximately 7 inches by about 3 inches have been found to be a convenient size. Typically, the foam comprises 20–35% by weight based on the final composition.

The folowing non-limitative examples more particularly illustrate the present invention:

EXAMPLE 1

Strips of polyurethane foam, approximately 0.085 inches thick, were impregnated using a laboratory roller coater with a mixture of di-(hydrogenated tallow) dimethyl ammonium methyl sulfate (Varisoft 137 from Sherex Chemical Co.) and a polyethylene glycol 200 monostearate (Varonic 200MS from Sherex Chemical Co.) to which had been added zinc sulfate, alkyl benzyl dimethyl ammonium chloride and perfumes such that the final dried product contained the mixture of ingredients entrapped or entrained within the cellular structure of the foam and had a composition by weight of:

| | |
|---|---|
| Polyurethane foam | 27.27% |
| Varisoft 137 | 47.76% |
| Varonic 200MS | 20.47% |
| Zinc sulfate | 0.50% |
| Alkylbenzyl dimethyl ammonium chloride | 4.00% |
| Perfume added as desired | |

The thus impregnated product was allowed to dry in air, then cut into usable 3 inch by 7 inch sheets.

EXAMPLE 2

Following the procedure described in Example 1, the following product may be produced:

| | |
|---|---|
| Polyurethane foam | 27.27% |
| Varisoft 137 | 45.31% |
| Varonic 200MS | 19.42% |
| Sorbitol | 4.00% |
| Alkylbenzyl dimethyl ammonium chloride | 4.00% |
| Perfume added as desired | |

EXAMPLE 3

Following the procedure described in Example 1, the following product may be produced:

| | |
|---|---|
| Polyurethane foam | 27.27% |
| Varisoft 137 | 45.31% |
| Varonic 200MS | 19.42% |
| Dextrose | 4.00% |
| Alkylbenzyl dimethyl ammonium chloride | 4.00% |
| Perfume added as desired | |

EXAMPLE 4

Following the procedure described in Example 1, the alkyl benzyl dimethyl ammonium chloride may be substituted by Cetyl trimethyl ammonium bromide.

EXAMPLE 5

Following the procedure described in Example 1, the alkyl benzyl dimethyl ammonium chloride may be substituted by Cetyl dimethyl ethyl ammonium bromide.

What is claimed is:

1. An article useful for conditioning clothes in an automatic laundry dryer during the drying cycle which article comprises a flexible polyurethane foam substrate impregnated with or coated with an effective amount of a fabric conditioning agent, an effective amount of a halide ion-containing anti-microbial agent and an anti-discoloration-effective amount of zinc sulfate, sorbitol or dextrose.

2. An article according to claim 1 wherein the polyurethane foam is impregnated with the fabric conditioning agent, anti-microbial agent and anti-discoloration agent whereby they are entrapped or entrained within the cellular structure of the foam.

3. An article according to claim 1 wherein the fabric conditioning agent comprises a mixture of a cationic fabric softener present in an amount of 50-90% and a non-ionic surfactant present in an amount of 10-50%.

4. An article according to claim 3 wherein the fabric conditioning agent comprises a mixture of a cationic fabric softener present in an amount of 65-75% and a non-ionic surfactant present in an amount of 25-35%.

5. An article according to claim 1 wherein the fabric conditioning agent comprises a cationic fabric softener and a non-ionic surfactant present in a weight ratio of 1:1 to 9:1.

6. An article according to claim 1 wherein the fabric conditioning agent comprises a cationic fabric softener and a non-ionic surfactant present in a weight ratio of 1:1 to 2.3:1.

7. An article according to claim 1 wherein the fabric conditioning agent comprises a cationic fabric softener and a non-ionic surfactant present in a weight ratio of 70:30.

8. An article according to claim 1 wherein the fabric conditioning agent comprises a cationic fabric softener and a non-ionic surfactant present in a weight ratio of 85:15.

9. An article according to claim 3 wherein the non-ionic surfactant is a polyoxyethylene fatty acid ester of 12-18 carbon atoms in the fatty chain, a polyoxyethylene fatty alcohol ester of 12-18 carbon atoms in the fatty chain or a polyoxypropylene fatty acid ester of 12-18 carbon atoms in the fatty chain.

10. An article according to claim 7 wherein the cationic fabric softener is a quaternary ammonium fabric softener.

11. An article according to claim 10 wherein the cationic fabric softener is a dialkyl dimethyl ammonium methyl sulfate.

12. An article according to claim 11 wherein the dialkyl dimethyl ammonium methyl sulfate is di-(hydrogenated tallow) dimethyl ammonium methyl sulfate, distearyl dimethyl ammonium methyl sulfate, dipalmityl dimethyl ammonium methyl sulfate or dibehenyl dimethyl ammonium methyl sulfate.

13. An article according to claim 1 wherein the anti-discoloration agent is zinc sulfate, present in the amount of about 0.2% to about 2%.

14. An article according to claim 1 wherein the anti-discoloration agent is zinc sulfate, present in the amount of about 0.5%.

15. An article according to claim 1 wherein the anti-discoloration agent is sorbitol, present in the amount of about 2 to about 6%.

16. An article according to claim 1 wherein the anti-discoloration agent is sorbitol, present in the amount of about 4%.

17. An article according to claim 1 wherein the anti-discoloration agent is dextrose, present in the amount of about 2 to about 6%.

18. An article according to claim 1 wherein the anti-discoloration agent is dextrose, present in the amount of about 4%.

19. An article according to claim 1 wherein the halide ion-containing anti-microbial agent is a chloride, bromide or iodide ion-containing anti-microbial agent.

20. An article according to claim 1 wherein the halide ion-containing anti-microbial agent is a chloride ion-containing anti-microbial agent.

21. A method of conditioning clothes in an automatic laundry dryer during the drying cycle which method comprises placing in the dryer together with the clothes to be conditioned, a flexible polyurethane foam substrate impregnated with or coated with an effective amount of a fabric conditioning agent, an effective amount of a halide ion-containing anti-microbial agent and an anti-discoloration-effective amount of zinc sulfate, sorbitol or dextrose.

22. A method according to claim 21 wherein the polyurethane foam is impregnated with the fabric conditioning agent, anti-microbial agent and anti-discoloration agent whereby they are entrapped or entrained within the cellular structure of the foam.

23. A method according to claim 21 wherein the fabric conditioning agent comprises a mixture of a cationic fabric softener present in an amount of 50-90% and a non-ionic surfactant present in the amount of 10-50%.

24. A method according to claim 21 wherein the fabric conditioning agent comprises a mixture of a cationic fabric softener present in an amount of 65–75% and a non-ionic surfactant present in the amount of 25–35%.

25. A method according to claim 21 wherein the fabric conditioning agent comprises a cationic fabric softener and a non-ionic surfactant present in a weight ratio of 1:1 to 9:1.

26. A method according to claim 21 wherein the fabric conditioning agent comprises a cationic fabric softener and a non-ionic surfactant present in a weight ratio of 1:1 to 2.3:1.

27. A method according to claim 21 wherein the fabric conditioning agent comprises a cationic fabric softener and a non-ionic surfactant present in a weight ratio of 70:30.

28. A method according to claim 21 wherein the fabric conditioning agent comprises a cationic fabric softener and a non-ionic surfactant present in a weight ratio of 85:15.

29. A method according to claim 21 wherein the non-ionic surfactant is a polyoxyethylene fatty acid ester of 12–18 carbon atoms in the fatty chain, a polyoxyethylene fatty alcohol ester of 12–18 carbon atoms in the fatty chain or a polyoxypropylene fatty acid ester of 12–18 carbon atoms in the fatty chain.

30. A method according to claim 27 wherein the cationic fabric softener is a quaternary ammonium fabric softener.

31. A method according to claim 30 wherein the cationic fabric softener is a dialkyl dimethyl ammonium methyl sulfate.

32. A method according to claim 31 wherein the dialkyl dimethyl ammonium methyl sulfate is di-(hydrogenated tallow) dimethyl ammonium methyl sulfate, distearyl dimethyl ammonium methyl sulfate, dipalmityl dimethyl ammonium methyl sulfate or dibehenyl dimethyl ammonium methyl sulfate.

33. A method according to claim 21 wherein the anti-discoloration agent is zinc sulfate, present in the amount of about 0.2% to about 2%.

34. A method according to claim 21 wherein the anti-discoloration agent is zinc sulfate, present in the amount of about 0.5%.

35. A method according to claim 21 wherein the anti-discoloration agent is sorbitol, present in the amount of about 2 to about 6%.

36. A method according to claim 21 wherein the anti-discoloration agent is sorbitol, present in the amount of about 4%.

37. A method according to claim 21 wherein the anti-discoloration agent is dextrose, present in the amount of about 2 to about 6%.

38. A method according to claim 21 wherein the anti-discoloration agent is dextrose, present in the amount of about 4%.

39. A method according to claim 21 wherein the halide ion-containing anti-microbial agent is a chloride, bromide or iodide ion-containing anti-microbial agent.

40. A method according to claim 21 wherein the halide ion-containing anti-microbial agent is a chloride ion-containing anti-microbial agent.

* * * * *